(12) United States Patent
Zhang

(10) Patent No.: US 11,488,463 B1
(45) Date of Patent: Nov. 1, 2022

(54) CO ALARM FOR SUPER CAPACITANCE TYPE GENERATOR

(71) Applicant: Shaoxing Dushang Yicheng Electric Machinery Co., Ltd., Zhejiang (CN)

(72) Inventor: Wangfu Zhang, Zhejiang (CN)

(73) Assignee: Shaoxing Dushang Yicheng Electric Machinery Co., Ltd., Shaoxing (CN)

( * ) Notice: Subject to any disclaimer, the term of this patent is extended or adjusted under 35 U.S.C. 154(b) by 0 days.

(21) Appl. No.: 17/489,803

(22) Filed: Sep. 30, 2021

(30) Foreign Application Priority Data

Jun. 23, 2021 (CN) .......................... 202110698662.0

(51) Int. Cl.
- *G08B 21/14* (2006.01)
- *H02J 7/34* (2006.01)
- *G08B 25/10* (2006.01)
- *G01G 11/18* (2006.01)
- *G01N 33/00* (2006.01)

(52) U.S. Cl.
CPC ............. *G08B 21/14* (2013.01); *G01G 11/18* (2013.01); *G08B 25/10* (2013.01); *H02J 7/345* (2013.01); *G01N 33/004* (2013.01)

(58) Field of Classification Search
CPC ........ G08B 21/14; G08B 25/10; G01G 11/18; G01N 33/004
See application file for complete search history.

(56) References Cited

U.S. PATENT DOCUMENTS

| | | | |
|---|---|---|---|
| 10,319,207 B1* | 6/2019 | Janscha | G01N 33/004 |
| 2009/0051551 A1* | 2/2009 | Pham | G08B 17/113 |
| | | | 340/577 |
| 2015/0159563 A1* | 6/2015 | Soni | F02C 7/228 |
| | | | 60/773 |
| 2017/0184560 A1* | 6/2017 | Crescini | G01N 33/0031 |
| 2020/0040827 A1* | 2/2020 | Janscha | G01N 33/004 |
| 2020/0242916 A1* | 7/2020 | Krstanovic | G08B 25/10 |
| 2020/0342730 A1* | 10/2020 | Liu | G08B 17/06 |
| 2021/0100291 A1* | 4/2021 | Sur | A24F 40/57 |
| 2021/0225145 A1* | 7/2021 | Badri | G08B 21/14 |

\* cited by examiner

*Primary Examiner* — Ojiako K Nwugo

(57) ABSTRACT

The present invention discloses a CO alarm for a super capacitance type generator, comprising a MCU control unit U1, a communication unit U2, a voltage reference unit U3, a system power supply unit U4, an alarm indication unit U5, an engine operation detection unit U6, a CO sensor detection unit U7, a super-capacitor charging unit U8, a temperature detection unit U9, and a flameout control unit U10. The MCU control unit U1 is configured to analyze and process the signal of the entire alarm and control the corresponding actions, and includes a single-chip microcomputer IC1 and a capacitor C1. The capacitor C1 is a filter capacitor, which filters the power supply voltage of the single-chip microcomputer IC1.

10 Claims, 7 Drawing Sheets

CO ALARM FOR SUPER CAPACITANCE TYPE GENERATOR

CROSS REFERENCE TO RELATED APPLICATIONS

The present application claims the benefit of Chinese Patent Application No. 202110698662.0 filed on Jun. 23, 2021, the contents of which are incorporated herein by reference in their entirety.

TECHNICAL FIELD

The present invention relates to the technical field of CO alarms, and in particular to a CO alarm for a super capacitance type generator.

BACKGROUND

Portable generators are widely used because of their small size, mobility, and strong adaptability to the working environment, etc. However, because this type of generator drives a magneto to output power using a gasoline engine, a large amount of CO harmful gas will be generated during use. In many household applications, many accidents of casualties happen because of ignoring the CO emission problems. In many countries, to meet the safety requirements, mandatory installation of CO alarms has been implemented. In order to meet the market demands, the present invention provides a CO alarm for a super capacitance type generator.

SUMMARY

In order to overcome the shortcomings of the prior art, the present invention provides a CO alarm for a super capacitance type generator.

In order to achieve the above object, the present invention adopts the following technical solutions. A CO alarm for a super capacitance type generator, comprising:
- a MCU control unit U1, configured to analyze and process the signal of the entire alarm, and control the corresponding actions;
- a communication unit U2, configured to send and receive information with an external carrier;
- a system power supply unit U4, configured to provide the working power required by the MCU control unit U1;
- an alarm indication unit U5, configured to give an alarm prompt for the CO concentration and an alarm failure prompt;
- an engine operation detection unit U6, configured to collect the working status of the generator;
- a CO sensor detection unit U7, configured to convert the CO concentration in the environment into a corresponding electrical signal, and output to the MCU control unit U1 for processing;
- a super-capacitor charging unit U8 that is connected to the system power supply unit U4, configured to provide the required power supply to the MCU control unit U1 by a super-capacitor when the system power supply unit stops supplying power;
- a temperature detection unit U9, configured to collect the ambient temperature to compensate for the change of the sensor detection unit U7 caused by change of temperature;
- a flameout control unit U10, configured to shut down the generator when the alarm fails or the CO concentration alarms;
- a voltage reference unit U3, configured to provide a reference voltage for the MCU control unit U1 and provide a forward bias for a sensor detection unit U8;

when the generator generates excessive CO, the CO concentration in the environment is converted into a corresponding electrical signal by the CO sensor detection unit U7 to output to the MCU control unit U1 for processing. After processing by the MCU control unit U1, the signal is sent to the alarm indication unit U5 and the flameout control unit U10, to give an alarm prompt of the CO concentration and shut down the generator, thereby preventing safety accidents; and when the system power supply unit stops supplying power, the super-capacitor charging unit U8 can provide the required power supply for the MCU control unit U1, to further ensure the stability of the alarm.

Preferably, the super-capacitor charging unit U8 comprises a rectifier bridge D5, a resistor R17, a capacitor C3, a capacitor C21, a super-capacitor C9, a resistor R18, a diode D6, a transistor Q2, a resistor R32 and a diode D3.

Preferably, the CO sensor detection unit U7 comprises a sensor J1, a CO sensor anti-polarization circuit, a sensor self-checking circuit, a potentiostat circuit, an operational amplifier circuit, a capacitor C17, a resistor R9, a capacitor C7, and a capacitor C11.

Preferably, the sensor J1 is a tripolar electrochemical sensor.

Preferably, the communication unit U2 comprises a resistor R6, a resistor R24, a MOS transistor Q4, a resistor R31 and a capacitor C4.

Preferably, the MCU control unit U1 comprises a single-chip microcomputer IC1 and a capacitor C1.

Preferably, the flameout control unit U10 comprises a resistor R3, a photocoupler IC2, a resistor R4 and a transistor Q3.

Preferably, the temperature detection unit U9 comprises a chip IC4, a capacitor C18, a resistor R26 and a capacitor C18.

In summary, when the generator produces excessive CO, the CO concentration in the environment is converted into a corresponding electrical signal by the CO sensor detection unit U7 to output to the MCU control unit U1 for processing. After processing by the MCU control unit U1, the signal is sent to the alarm indication unit U5 and the flameout control unit U10, to give an alarm prompt of the CO concentration and shut down the generator, thereby preventing safety accidents; and when the system power supply unit stops supplying power, the super-capacitor charging unit U8 can provide the required power supply for the MCU control unit U1, to further ensure the stability of the alarm.

DETAILED DESCRIPTION

Figure 1:
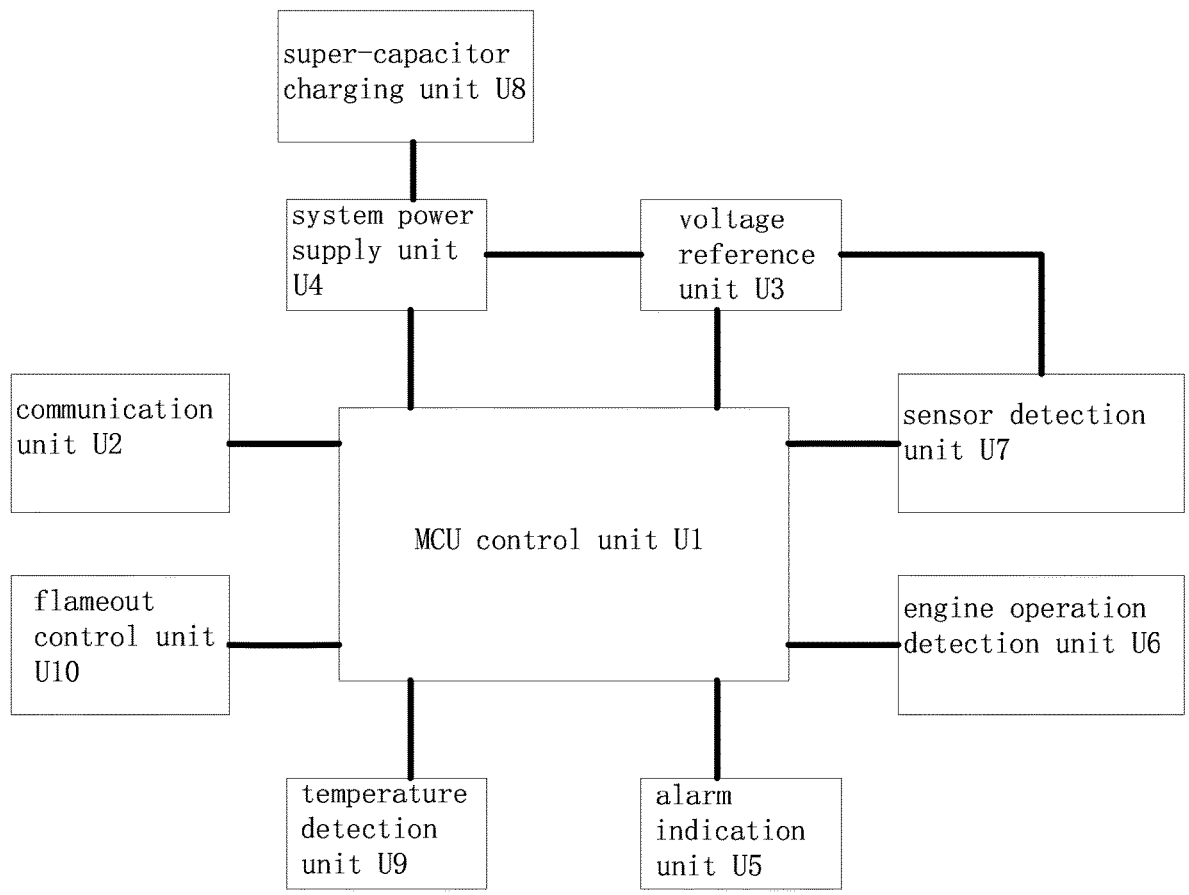
FIG. 1 is a structural representation of the present invention.
Figure 2:
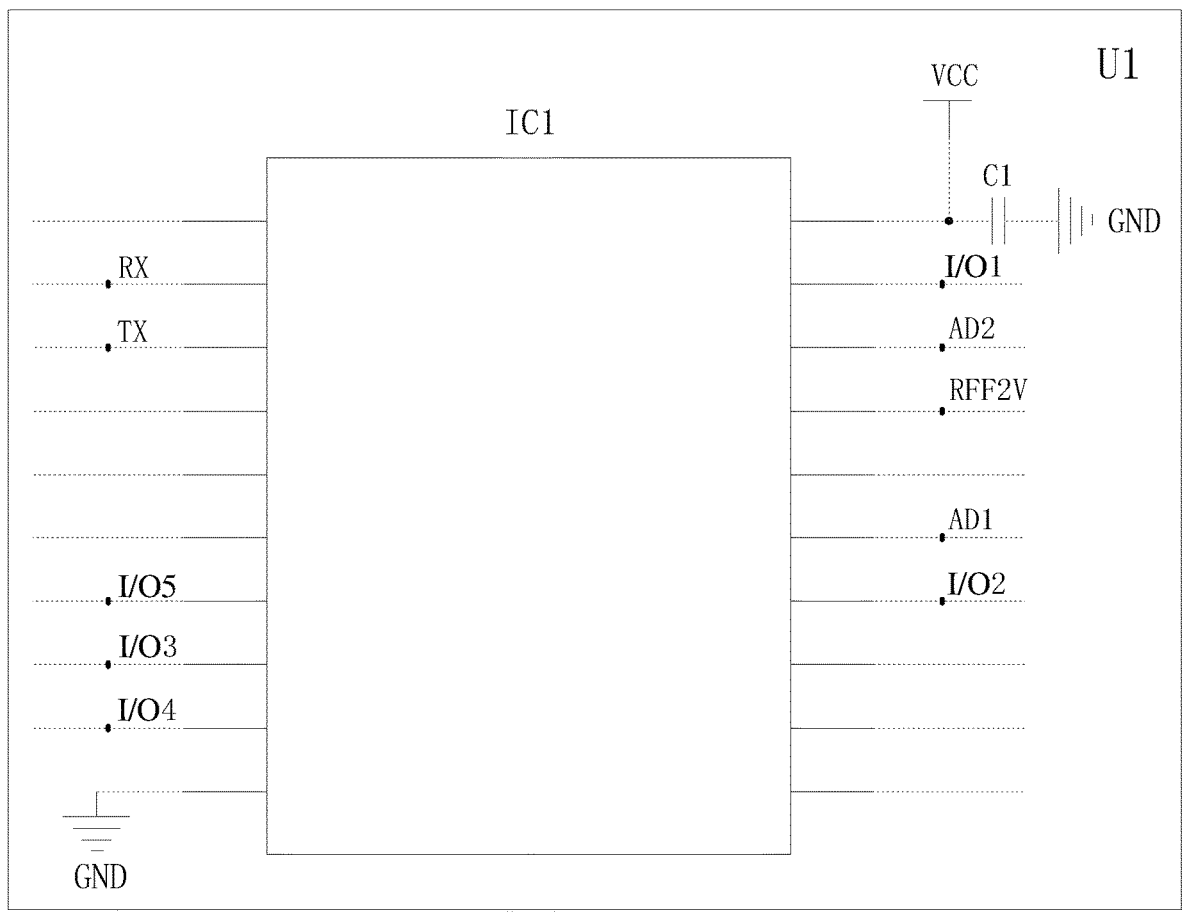
FIG. 2 is a circuit diagram of a MCU control unit U1.
Figure 3:
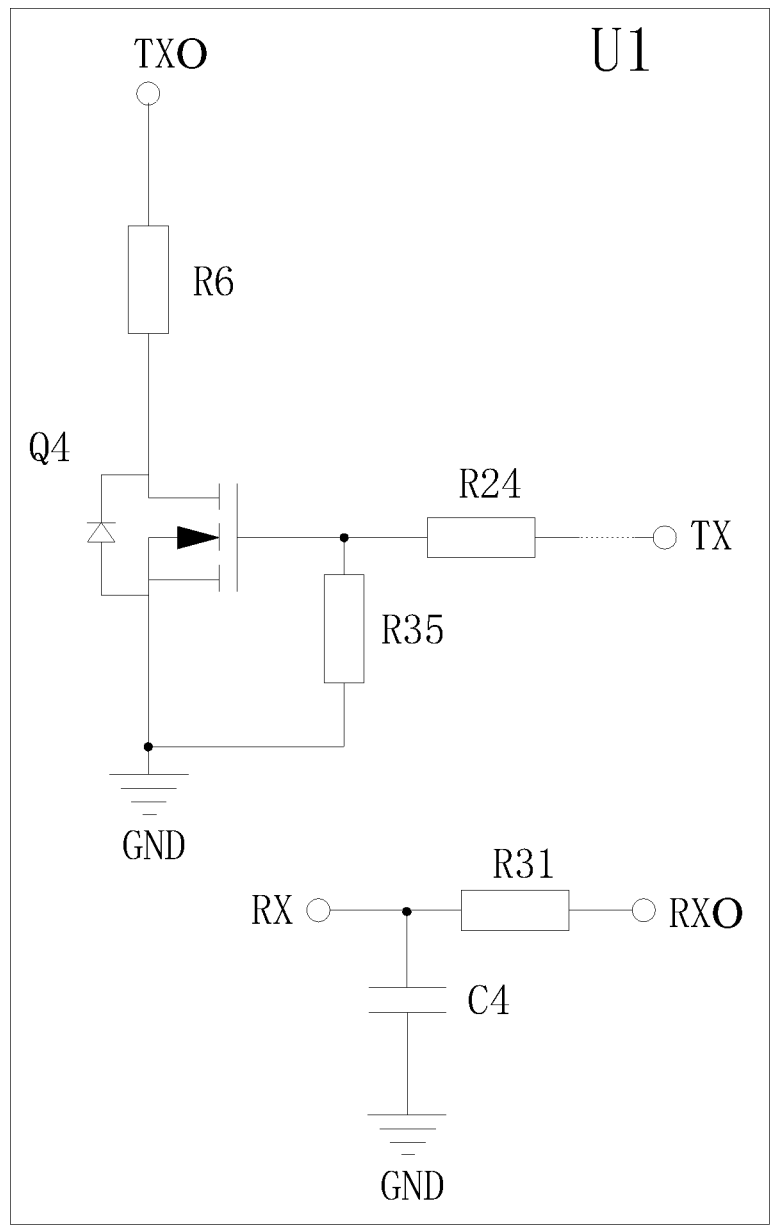
FIG. 3 is a circuit diagram of a communication unit U2.
Figure 4:
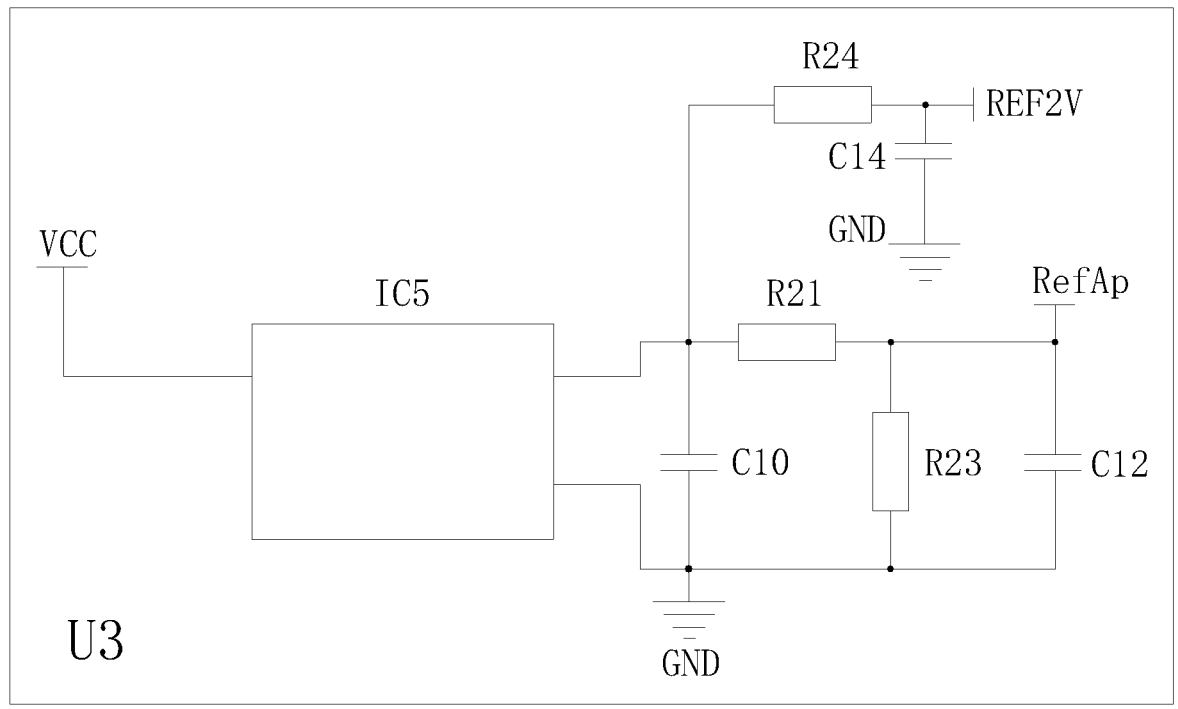
FIG. 4 is a circuit diagram of a voltage reference unit U3.
Figure 5:
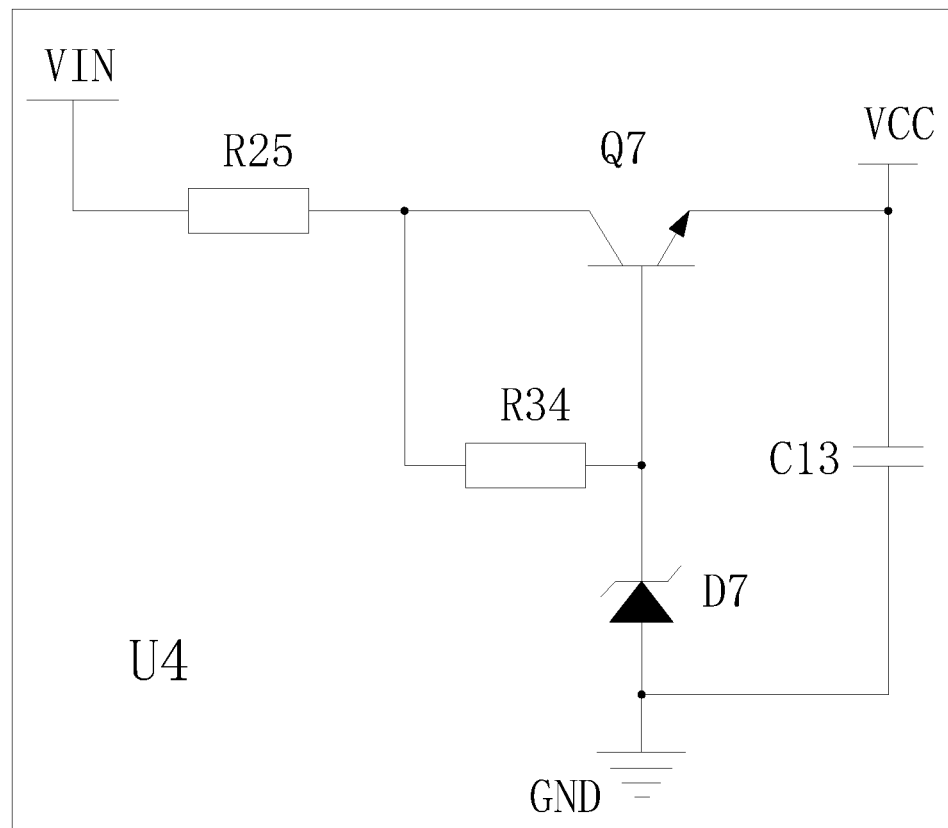
FIG. 5 is a circuit diagram of a system power supply unit U4.
Figure 6:
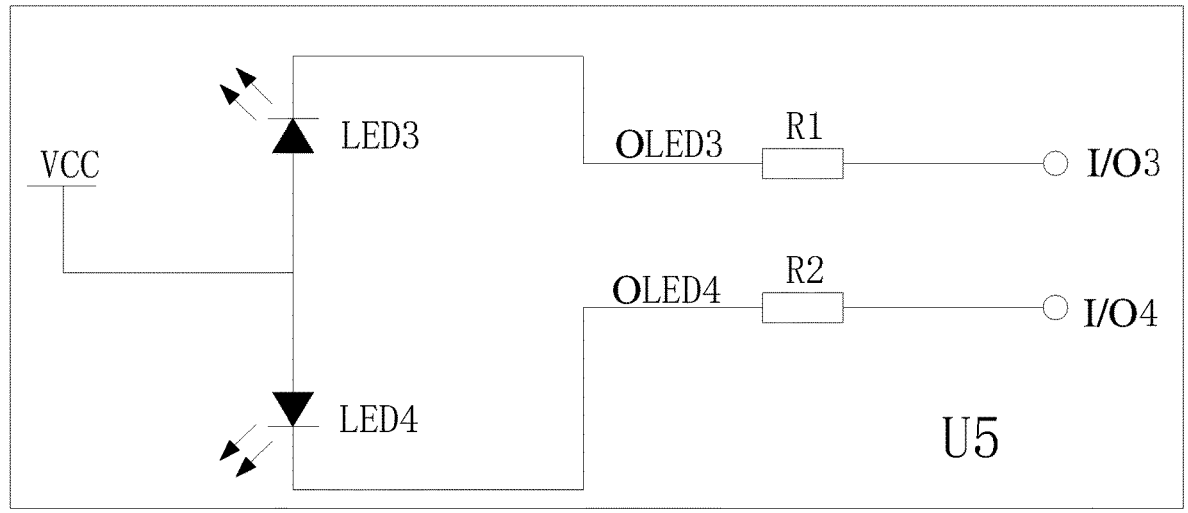
FIG. 6 is a circuit diagram of an alarm indication unit U5.
Figure 7:
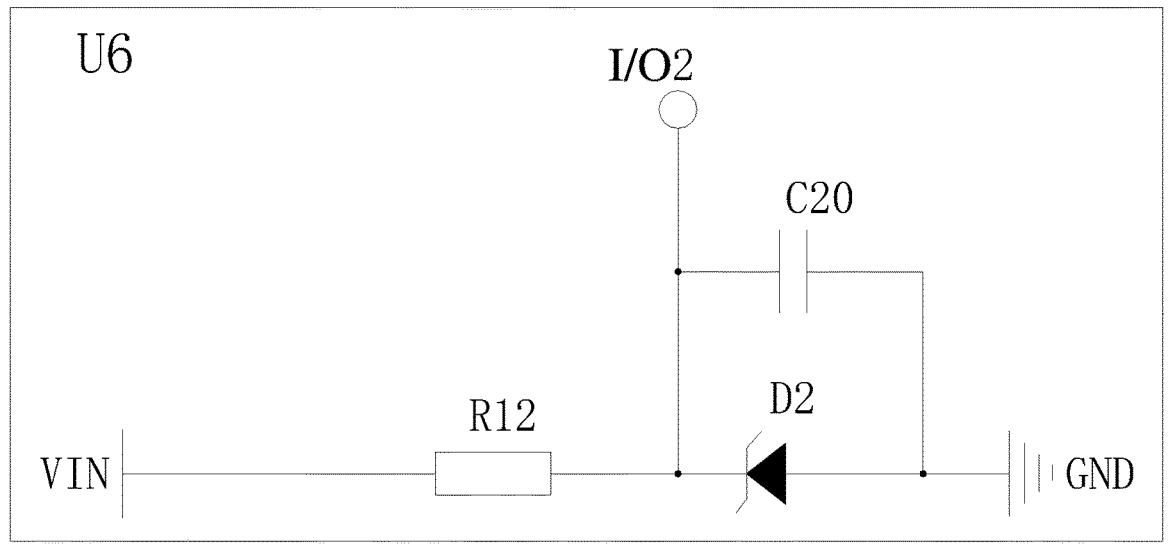
FIG. 7 is a circuit diagram of an engine operation detection unit U6.
Figure 8:
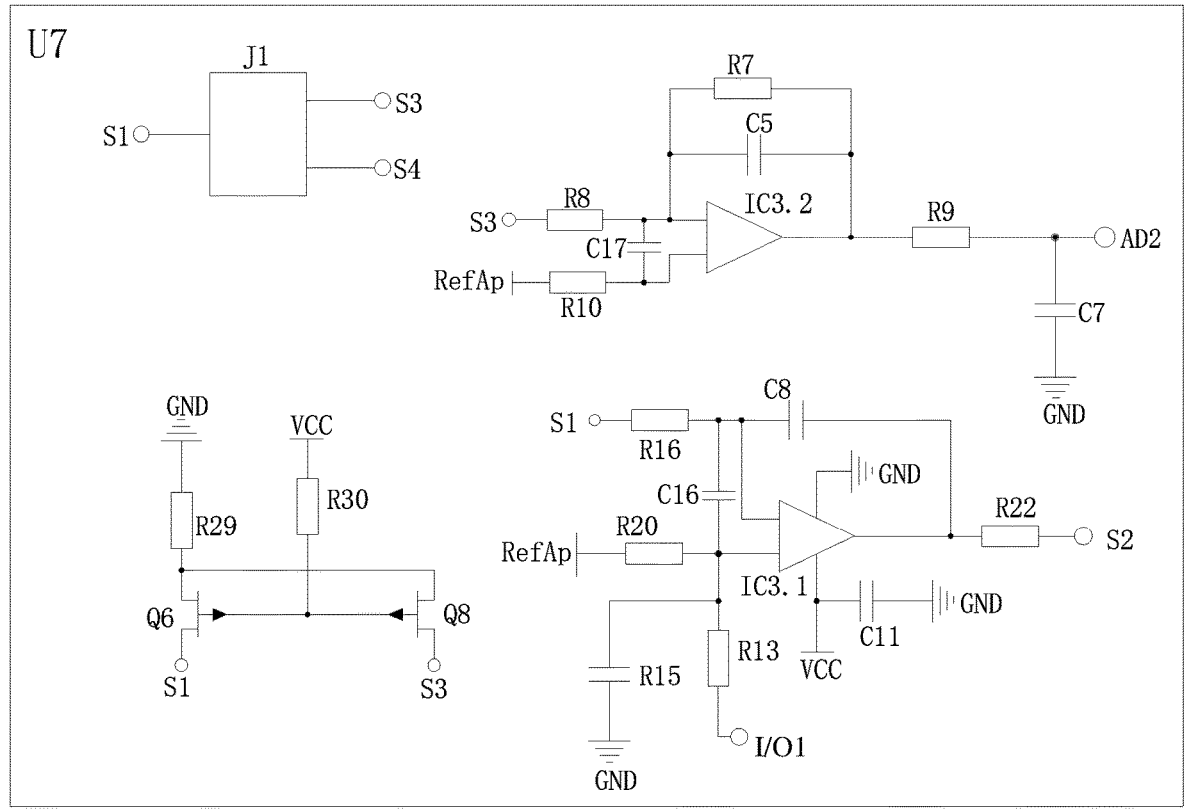
FIG. 8 is a circuit diagram of a CO sensor detection unit U7.
Figure 9:
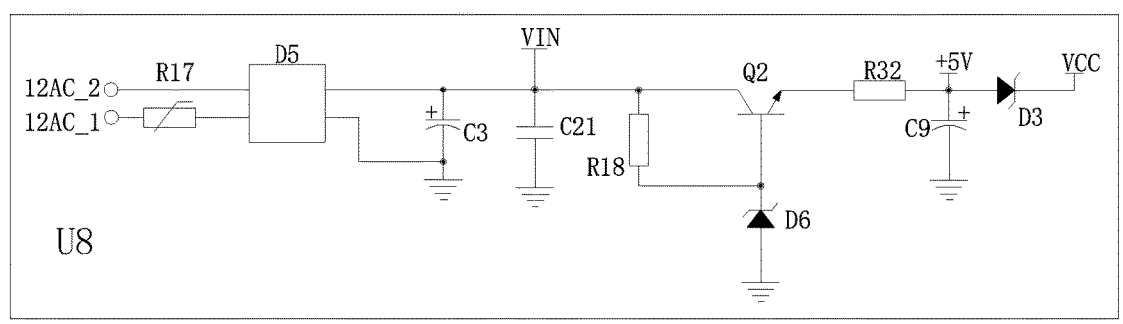
FIG. 9 is a circuit diagram of a super-capacitor charging unit U8.
Figure 10:
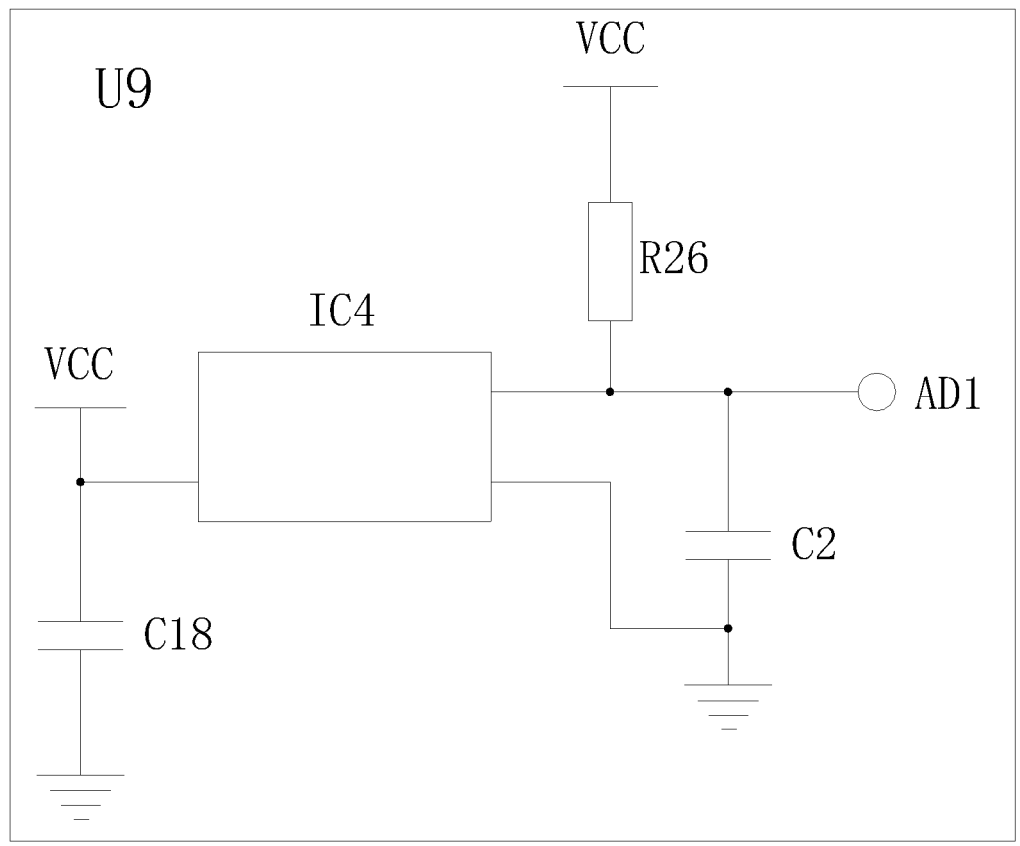
FIG. 10 is a circuit diagram of a temperature detection unit U9.
Figure 11:
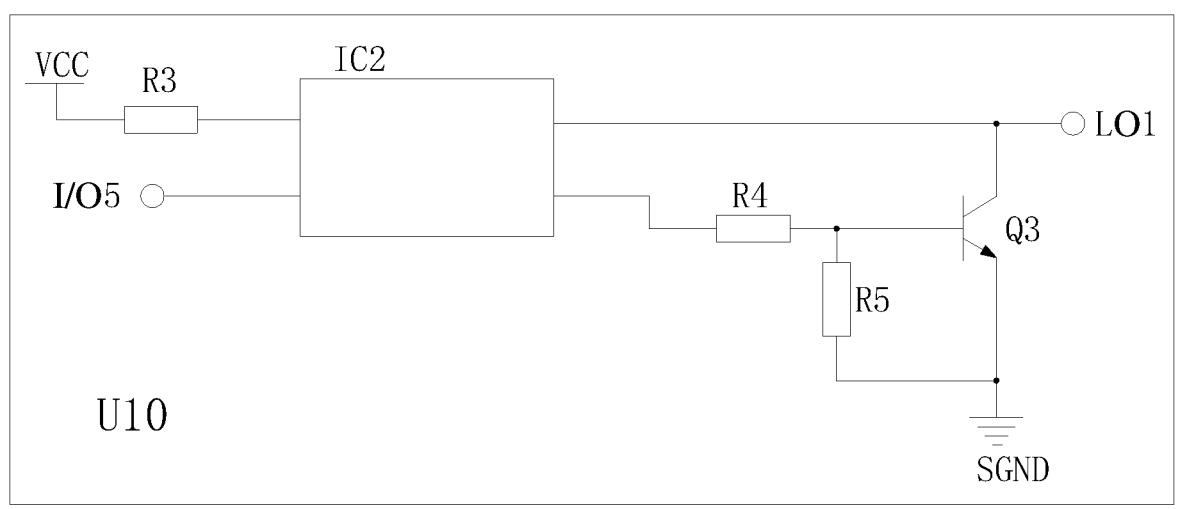
FIG. 11 is a circuit diagram of a flameout control unit U10.

As shown in FIGS. 1 to 11, a CO alarm for a super capacitance type generator is provided, comprising a MCU control unit U1, a communication unit U2, a voltage reference unit U3, a system power supply unit U4, an alarm indication unit U5, an engine operation detection unit U6, a CO sensor detection unit U7, a super-capacitor charging unit U8, a temperature detection unit U9 and a flameout control unit U10. The MCU control unit U1 is configured to analyze and process the signal of the entire alarm and control the corresponding actions, and it includes a single-chip microcomputer IC1 and a capacitor C1. The capacitor C1 is a filter capacitor, which filters the power supply voltage of the single-chip microcomputer ICE Specifically, the communication unit U2 is configured to send and receive information with the external carrier, and it includes a resistor R6, a resistor R24, a resistor R27, a MOS transistor Q4, a resistor R31, and a capacitor C4. The resistor R6 and resistor R24 are current-limiting resistors. The resistor R27 provides a low potential bias for the base of the MOS transistor Q4 to prevent the MOS transistor Q4 from being triggered by mistake; the signal sent by the TX pin of the single-chip microcomputer IC1 is output to an external TXO through the MOS transistor Q4; the resistor R31 is a current-limiting resistor; the capacitor C4 is a filter capacitor, which filters the signal input from the external RXO, and then inputs it to the RX pin of the single-chip microcomputer IC1.

Specifically, the system power supply unit U4 is configured to provide the working power required by the MCU control unit U1, and it includes a resistor R25, a resistor R34, a transistor Q7, a diode D7, and a capacitor C13. The resistor R25 is a current-limiting resistor; the resistor R34 is a B pole bias resistor of the transistor Q7, which forms a voltage stabilizing circuit with the diode D7; the diode D7 is a voltage stabilizing diode to ensure that the output voltage VCC of the E pole of the transistor Q7 is stable; the capacitor C13 is a filter capacitor, to perform filtering of VCC.

Specifically, the alarm indication unit U5 is configured to give an alarm prompt for the CO concentration and an alarm failure prompt, and it includes a lamp LED4, a lamp LED3, a resistor R1 and a resistor R2. The resistor R1 and resistor R2 are current-limiting resistors; the lamp LED4 is a red lamp, which is configured to give CO gas concentration alarm indication, including CO peak concentration alarm indication and CO average concentration alarm indication; the lamp LED3 is a yellow lamp, which is configured to give a module fault alarm indication, and the faults include super-capacitor faults, alarm high-temperature fault indication, and sensor fault indication, etc.

Specifically, the engine operation detection unit U6 is configured to collect the working status of the generator, and it includes a resistor R1, a diode D2, and a capacitor C20. The resistor R12 is a current-limiting resistor, and the diode D2 is a voltage stabilizing diode, and they constitute a voltage stabilizing output circuit, to ensure that the voltage input to the I/O2 pin of the single-chip microcomputer IC1 will not be higher than the voltage stabilization value of the diode D2; the capacitor C20 is a filter capacitor, which performs filtering on the voltage input to the I/O2 pin of the single-chip microcomputer IC1.

Specifically, the CO sensor detection unit U7 is configured to convert the CO concentration in the environment into a corresponding electrical signal, and output to the MCU control unit U1 for processing, and it includes a sensor J1, a CO sensor anti-polarization circuit, a sensor self-checking circuit, a potentiostat circuit, an operational amplifier circuit, a capacitor C17, a resistor R9, a capacitor C7 and a capacitor C11. The sensor J1 is a tripolar electrochemical sensor; the sensor anti-polarization circuit is composed of a resistor R29, a resistor R30, a J-type field effect transistor Q6 and a J-type field effect transistor Q8; the sensor self-checking circuit is composed of a resistor R13, a capacitor C15, and an I/O1 pin of a single-chip microcomputer IC1; the potentiostat circuit includes a resistor R20, a resistor R16, a resistor R22, a capacitor C8, a capacitor C16 and a chip IC3.1, which adds a constant potential between the working electrode and the reference electrode of the sensor J1 to maintain the electrochemical stability of sensor J1 and enable the sensor to stably output analog signals; the operational amplifier circuit is composed of a resistor R8, a resistor R10, a resistor R7, a capacitor C5, a capacitor C19, an operational amplifier IC3_1 and an operational amplifier IC3_2, which amplifies and outputs the electrical signal output by the sensor J1 to a pin AD2 of single-chip microcomputer IC1; the capacitor C17 is a filter capacitor, which can filter the output signal of the sensor J1; the resistor R9 and capacitor C7 filter the signal output by the operational amplifier IC3_2; the capacitor C11 filters the power supply of the operational amplifier IC3_1 and the operational amplifier IC3_2.

Specifically, the super-capacitor charging unit U8 includes a rectifier bridge D5, a resistor R17, a capacitor C3, a capacitor C21, a super-capacitor C9, a resistor R18, a diode D6, a transistor Q2, a resistor R32, and a diode D3. The resistor R17 is a thermistor, playing a role of current limiting; the capacitor C3 and capacitor C21 store and filter the voltage output by the rectifier bridge D5; the resistor R18, diode D6, and transistor Q2 can form a series voltage stabilizing circuit; the diode D6 provides a voltage stabilization reference; the resistor R32 is a super-capacitor charging current-limiting resistor; the capacity of the super-capacitor C9 can be selected according to the actual power consumption and service life; the diode D3 prevents the reverse input of the VCC power supply.

Specifically, the temperature detection unit U9 includes a chip IC4, a capacitor C18, a resistor R26, and a capacitor C18. The chip IC4 is a temperature sensor chip for detecting the ambient temperature; the capacitor C18 is a filter capacitor for filtering the input power VCC; the resistor R26 is a pull-up resistor; the capacitor C2 is a filter capacitor, which filters the signal output by the chip IC4, and then outputs it to the AD1 port of the single-chip microcomputer IC1.

Specifically, the flameout control unit U10 is configured to shut down the generator when the alarm fails or the CO concentration alarms, and it includes a resistor R3, a photocoupler IC2, a resistor R4, and a transistor Q3. The resistor R3 is a current-limiting resistor; the resistor R4 is a current-limiting resistor; the resistor R5 is a pull-down bias resistor of the transistor Q3 to prevent false triggering of the transistor Q3; the I/O5 of the single-chip microcomputer IC1 controls the ON/OFF of the photocoupler IC2, thereby controlling the ON/OFF of the transistor Q3, and then controls the ignition trigger voltage at LO1 to be directly connected to the ground, to achieve the purpose of igniter flameout.

Specifically, the voltage reference unit U3 is configured to provide a reference voltage for the MCU control unit U1 and provide the forward bias for the sensor detection unit U8, and it includes a chip IC5, a resistor R19, a capacitor C14, a resistor R21, a resistor R23, a capacitor C10 and a capacitor C12. The chip IC5 is a voltage reference chip, the reference voltage is sent to the REF2V pin of the single-chip microcomputer IC1 through a filter circuit composed of the resistor R19 and the capacitor C14, and the ratio of the resistor R21 and the resistor R23 determines the voltage of RefAP; the capacitor C10 and capacitor C12 are filter capacitors, the capacitor C10 filters the reference voltage output by the chip, and the capacitor C12 filters the formed RefAP voltage; the VCC provides voltage reference power supply for the chip IC5, and REF2V is input to the REF2V of the single-chip microcomputer IC1, which is the ADC sampling voltage reference of the single-chip microcomputer IC1; RefAP is input to the operational amplifiers IC3_1 and IC3_2 in the CO sensor detection unit U7, to provide a forward bias for the operational amplifiers IC3_1 and IC3_2.

What is claimed is:

1. A CO alarm for a super capacitance type generator, comprising:
    a MCU control unit (U1), configured to analyze and process the signal of the entire alarm, and control the corresponding actions;
    a communication unit (U2), configured to send and receive information with an external carrier;
    a system power supply unit (U4), configured to provide the working power required by the MCU control unit (U1);
    an alarm indication unit (U5), configured to give an alarm prompt for the CO concentration and an alarm failure prompt;
    an engine operation detection unit (U6), configured to collect the working status of the generator;
    a CO sensor detection unit (U7), configured to convert the CO concentration in the environment into a corresponding electrical signal, and output to the MCU control unit (U1) for processing;
    a super-capacitor charging unit (U8) that is connected to the system power supply unit (U4), configured to provide the required power supply to the MCU control unit (U1) by a super-capacitor when the system power supply unit stops supplying power;
    a temperature detection unit (U9), configured to collect the ambient temperature to compensate for the change of the sensor detection unit (U7) caused by change of temperature;
    a flameout control unit (U10), configured to shut down the generator when the alarm fails or the CO concentration alarms;
    a voltage reference unit (U3), configured to provide a reference voltage for the MCU control unit (U1) and provide a forward bias for a sensor detection unit (U8);
    wherein, the CO sensor detection unit (U7) comprises a sensor (J1), a CO sensor anti-polarization circuit, a sensor self-checking circuit, a potentiostat circuit, an operational amplifier circuit, a first capacitor (C17), a first resistor (R9), a second capacitor (C7), and a third capacitor (C11).

2. The CO alarm for a super capacitance type generator according to claim 1, wherein the super-capacitor charging unit (U8) comprises a rectifier bridge (D5), a second resistor (R17), a fourth capacitor (C3), a fifth capacitor (C21), a super-capacitor (C9), a third resistor (R18), a first diode (D6), a first transistor (Q2), a fourth resistor (R32) and a second diode (D3).

3. The CO alarm for a super capacitance type generator according to claim 1, wherein the potentiostat circuit comprises a fifth resistor (R20), a sixth resistor (R16), a seventh resistor (R22), a sixth capacitor (C8), a seventh capacitor (C16) and a first chip (IC3.1).

4. The CO alarm for a super capacitance type generator according to claim 1, wherein the sensor (J1) is a tripolar electrochemical sensor.

5. The CO alarm for a super capacitance type generator according to claim 1, wherein the communication unit (U2) comprises an eighth resistor (R6), a ninth resistor (R24), a MOS transistor (Q4), a tenth resistor (R31) and an eighth capacitor (C4).

6. The CO alarm for a super capacitance type generator according to claim 1, wherein the MCU control unit (U1) comprises a single-chip microcomputer (IC1) and a ninth capacitor (C1).

7. The CO alarm for a super capacitance type generator according to claim 1, wherein the flameout control unit (U10) comprises an eleventh resistor (R3), a photocoupler (IC2), a twelfth resistor (R4) and a second transistor (Q3).

8. The CO alarm for a super capacitance type generator according to claim 1, wherein the temperature detection unit (U9) comprises a second chip (IC4), a tenth capacitor (C18), a thirteenth resistor (R26) and an eleventh capacitor (C18).

9. The CO alarm for a super capacitance type generator according to claim 1, wherein the voltage reference unit (U3) comprises a third chip (IC5), a fourteenth resistor (R19), a twelfth capacitor (C14), a fifteenth resistor (R21), a sixteenth resistor (R23), a thirteenth capacitor (C10) and a fourteenth capacitor (C12).

10. The CO alarm for a super capacitance type generator according to claim 1, wherein the alarm indication unit (U5) comprises a first lamp (LED4), a second lamp (LED3), a seventeenth resistor (R1) and an eighteenth resistor (R2).

* * * * *